United States Patent [19]

Brisson

[11] Patent Number: 4,930,509

[45] Date of Patent: Jun. 5, 1990

[54] X-RAY AIMING FIXTURE

[75] Inventor: Alfred G. Brisson, Kildeer, Ill.

[73] Assignee: Northgate Research, Inc., Arlington Heights, Ill.

[21] Appl. No.: 300,370

[22] Filed: Jan. 23, 1989

[51] Int. Cl.[5] .......................... A61B 6/00; A61B 17/22
[52] U.S. Cl. ..................................... 128/653; 606/128; 128/24 A; 378/205
[58] Field of Search ........................... 128/24 EL, 653; 606/127, 128; 378/62, 99, 162, 205; 358/111

[56] References Cited

U.S. PATENT DOCUMENTS

| | | | |
|---|---|---|---|
| 4,418,422 | 11/1983 | Richter et al. | 378/205 |
| 4,705,026 | 11/1987 | Chaussy et al. | 128/24 A |
| 4,764,944 | 8/1988 | Finlayson | 378/205 |
| 4,803,976 | 2/1989 | Frigg et al. | 378/205 |

*Primary Examiner*—Max Hindenburg
*Assistant Examiner*—Kevin L. Pontius
*Attorney, Agent, or Firm*—Robert M. Wolters

[57] ABSTRACT

A lithotripter is provided with an x-ray aiming system. The lithotripter includes an upwardly opening ellipsoidal reflector having a vertical axis. This reflector is supported from a pedestal, and an arm rigid with the pedestal supports a radio opaque disc which is disposed below overhead x-ray apparatus. A patient with a kidney stone is disposed on a table above the reflector and below the x-ray apparatus. If the vertical axis of the reflector is perfectly aligned with the kidney stone in the patient, then the radio opaque disc will shadow the kidney stone, and provide positive evidence of alignment. If there is misalignment, then simple examination of the x-ray picture will show in what direction the reflector support, and hence the radio opaque disc, need be moved to effect proper alignment.

8 Claims, 1 Drawing Sheet

U.S. Patent    Jun. 5, 1990    4,930,509
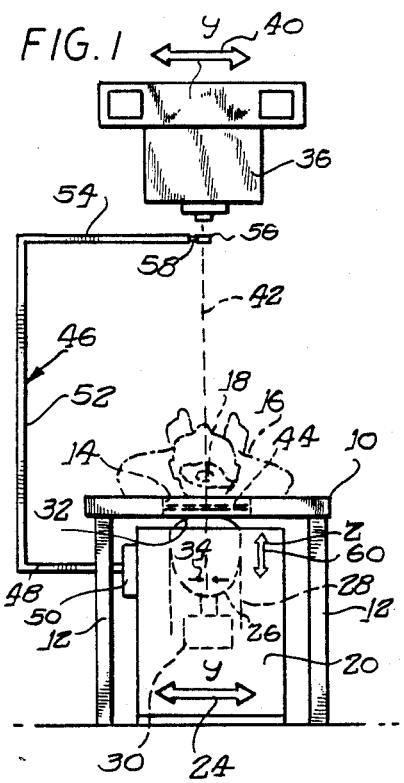
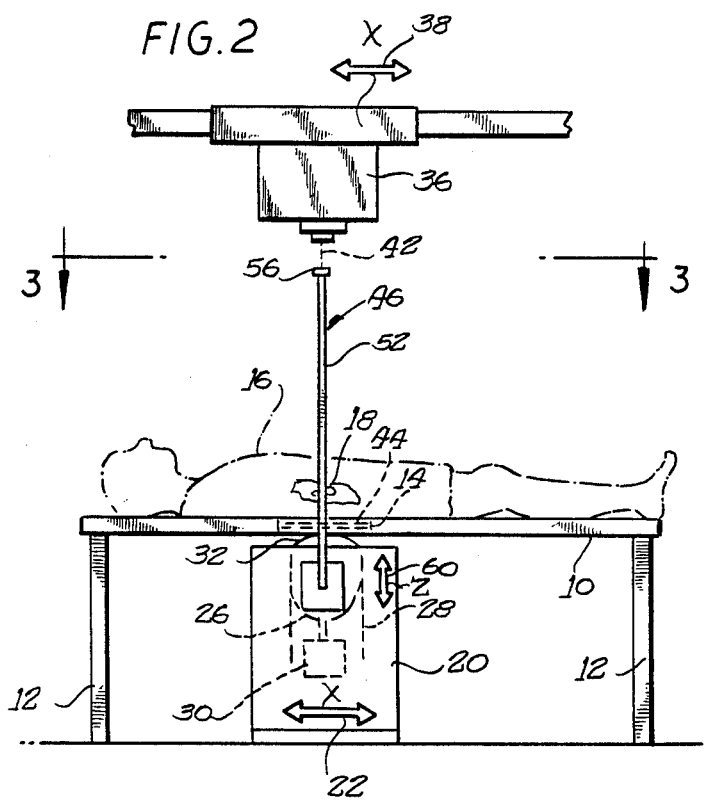
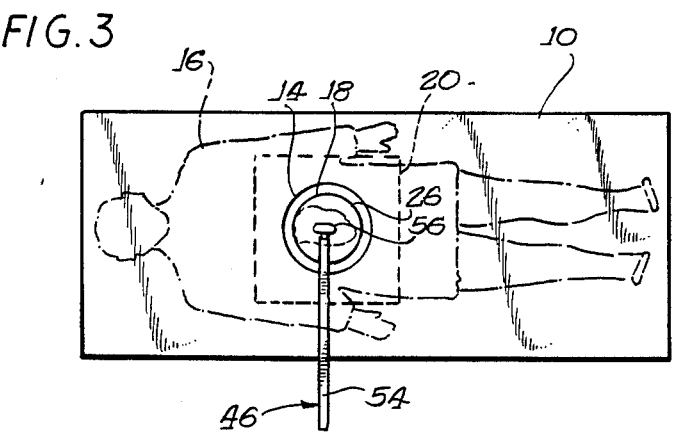

X-RAY AIMING FIXTURE

BACKGROUND OF THE INVENTION

Kidney stones, and also naturally-occurring stones in the bladder and the ureter can be exquisitely painful, and often require surgical relief. Excision or destruction of stones in the bladder and sometimes in the ureter can be relatively easily accomplished, but removal of stones from the kidney is a major procedure.

Surgical removal of stones from the kidney is a very serious and traumatic procedure. A large incision is made in the body. The kidney is essentially removed from the body and cut open. The stone or stones are then removed, whereupon the kidney is sutured and returned to the body with the body then being sutured. Typical recovery time is on the order of six to twelve months.

Chemotherapy is available as a noninvasive therapy for uric acid stones. In this therapy the urine is alkalized. The existing stone thus is dissolved over a substantial period of time, and in most cases the patient can be cured before this condition becomes acute. However the patient's condition is often already acute when the stone is discovered, and immediate removal is imperative. Attempts at chemical dissolution of other types of stones have not been successful.

More lately, extracorporeal distruction of kidney stones by means of lithotripters has become popular. With the use of earlier such machines as disclosed in Hoff et al U.S. Pat. Nos. 3,942,531 and Hausler 4,311,147 it has been necessary for the patient to be immersed in a tub of water in a crouched, face up position. Two dimensional x-ray procedures are utilized to determine the position of the stone by moving the patient. The machine includes an underwater spark gap shock wave generator which lies outside of the patient's body and at the first focus point of an ellipsoidal reflector. The patient is moved around in the water bath by several mechanisms until the kidney stone is positioned at the second focus point of the ellipsoid. A shock wave is then generated, and passes through the water bath and through the patient's body to convey the energy to the kidney stone. It will be apparent that precise aiming is necessary since the energy focused into an air or gas pocket in the body can cause damage to interface tissue, and in any event a misaimed shock wave has no effect on destruction of the kidney stone.

Some patients are reluctant to undergo x-ray aiming, and x-rays are not successful with certain types of stones that are not x-ray opague. Ultrasound devices have been used as an alternative as disclosed in Brisson, et al 4,763,652, assigned to the same assignee as the present application, namely Northgate Research Inc. of Arlington Heights, Ill. In accordance with Brisson et al, 4,763,652 the water bath is not necessary. A reflector is movable immediately adjacent to the body of the patient and is in contact with the patient's body through a diaphragm, the reflector being filled with water. Ultrasound transducers are used to locate the kidney stone, and the transducers are connected through a computer to motors for positioning the reflector relative to the patient so that the kidney stone in the patient will lie at the second focus point of the reflector. This system works remarkably well, but skill is necessary to read ultrasound images properly.

There is, therefore, a demand for an aiming system for a lithotripter which requires minimal reading skill, so that substantially any physician or technician can properly position the ellipsoidal reflector relative to the patient.

OBJECTS AND SUMMARY OF THE PRESENT INVENTION

It is an object of the present invention to provide a lithotripter which requires very little skill for proper aiming thereof.

More specifically, it is an object of the present invention to provide an x-ray aiming fixture in which a radio-opaque aiming point is rigid with the reflector and shadows the kidney stone in an x-ray picture when the reflector is properly aligned with the kidney stone.

In accordance with the present invention a table is provided on which the patient with the kidney stone lies. The table is provided with a hole therein and the patient is positioned with the kidney stone above this hole. A movable base or pedestal carries an upwardly directed, truncated ellipsoidal reflector which is positioned beneath the hole in the table. The reflector is filled with water, and a diaphram over the open end of the reflector is capable of projecting through the hole in the table to engage the patient's body in alignment with the kidney stone. Means is provided in the reflector in the form of a spark gap for generating a shock wave at the first focus point of the ellipsoidal reflector. The pedestal is movable horizontally across the floor to position the ellipsoidal reflector so that the second focus point thereof coincides with the kidney stone. A generally C-shaped arm extends out from the pedestal, then up, and then back horizontally to a position adjacent the x-ray generator. An opaque disc is disposed at the end of the arm. Conventional means is provided for positioning an x-ray film in the hole in the table, beneath the patient, and an x-ray is taken. If the pedestal is properly positioned, the disc, which is radio-opaque, shadows the kidney stone, and then it is known that the pedestal is in the right position in a horizontal plane. Additional means can be provided for positioning the ellipsoidal reflector vertically, such as known x-ray techniques, but the vertical positioning is much less critical, since the focus of the shock wave is along and within a cone of shallow taper in the vicinity of the second focus point of the ellipsoidal reflector, whereby precise positioning in the vertical plane is not critical.

THE DRAWINGS

The invention will best be understood with reference to the following description when taken in connection with the accompanying drawings wherein:

FIG. 1 is an end view of apparatus incorporating the x-ray aiming fixture of the present invention;

FIG. 2 is a side view taken at right angles to FIG. 1; and

FIG. 3 is a horizontal view taken substantially along the line 3—3 in FIG. 2.

DETAILED DESCRIPTION OF THE ILLUSTRATED EMBODIMENT

Turning now in greater particularity to the figures of the drawing, there will be seen a table 10 having upstanding legs 12. The table is provided with an aperture 14 of suitable shape thereby illustrated as being round. A patient 16 lies on the table 10 in such position that a kidney stone 18 is substantially centered over the hole in the table.

A pedestal 20 is disposed beneath the table and is horizontally movable in the X-plane as indicated by the arrow 22 in FIG. 2, and in the Y-plane as indicated by the arrow 24 in FIG. 1. In simplist terms the pedestal can simply slide across the floor as urged manually. It is obvious that rollers or casters can be provided to simplify rolling, but these should be of the type having brakes thereon for positively positioning the pedestal. A truncated, upwardly opening ellipsoidal reflector 26 is carried by the pedestal 20 and is vertically adjustable as in ways 28, a jack 30 being provided to effect the vertical adjustment. The reflector 26 is dimensioned so that it can be projected up into the opening or hole 14 so that a diaphram 32 overlying, and projecting above the open top of the reflector 26 may be pressed against the patient's body substantially in alignment with the kidney stone 18. A spark gap 34 of a type known in the art and supplied with electrical energy in accordance with known techniques (not shown) is disposed at the first focus point of the ellipsoidal reflector 26, and it is desired that the reflector should be positioned so that the kidney stone 18 is at the second focus point of the reflector.

An x-ray apparatus 36 is spaced a suitable distance above the table 10, and is supported in known means for movement in the horizontal plane in the X direction as indicated by the arrow 38 in FIG. 2, and in the Y direction as indicated by the arrow 40 in FIG. 1. The x-ray apparatus 36 directs an x-ray stream substantially straight down is indicated by the broken line 42. This x-ray stream passes through the patient's body, but not through the kidney stone, which is opaque.

Means is provided for supporting an x-ray film 44 beneath the patient's body. This may simply be a film holder lying on the table and spanning the opening 14, but more conveniently is in the form commonly used in which there is a drawer type device that can be slid across the opening and below the top surface of the table to position the x-ray film without disturbing the patient.

A substantially C-shaped arm or support 46 has a horizontal arm portion 48 secured to the side of the pedestal 20 at 50, and extending horizontally out from beneath the table 10. A verticle riser 52 extends up from the arm portion 48 displaced laterally from the table 10. At the top end of the riser 62 there is a horizontal arm portion 54 extending immediately below the x-ray apparatus 36 and nearly to the x-ray stream 42. A disc 56 is spaced outwardly from the end of the arm portion 54 by a support member 58 of restricted width. The disc 56 is radio-opaque and if the pedestal 20 is properly positioned, the disc will shadow the kidney stone 18 in the x-ray picture developed in the film 44. If the disc 56 does not perfectly shadow the kidney stone, then simple study of the x-ray will disclose in what direction, and precisely how far the pedestal 20 has to be moved so that the disc 56, which lies on the axis of the reflector 26, will perfectly shadow the kidney stone 18. A second x-ray picture preferably is made to ensure that the disc 56 does perfectly shadow the stone, whereby the reflector 26 is properly aligned with the stone.

It will be understood that the x-ray film and the support therefore have been removed following the second x-ray, whereby the jack 30 may raise the reflector 26 up into the opening 14 so the diaphram 32 will engage the patient's body properly to couple the shock wave energy from the reflector to the patient's body. Sparks jumping the gap 34 through the water in the reflector 26 then generate a series of shock waves, as is known. The shock waves focus on the kidney stone, and in a period of time reduce the kidney stone to small pieces that readily pass out of the body with the urine. The reflector 26 is adjusted vertically in the Z direction as indicated by the arrows 60 in order best to adjust the second focus point of the ellipsoid to lie precisely on the kidney stone 18. Insurance that the reflector is properly positioned in the Z direction may be confirmed by x-rays taken horizontally (not shown) or this position may be estimated rather accurately from the patient's body build and known location of the kidney stone from original diagnosis. It is to be understood that the maximum dimension of the reflector 26 in a horizontal direction is sufficiently smaller than the dimensions of the hole or opening 14 that the reflector can be moved adequately in the X and Y directions by movement of the pedestal 20 without impediment by the size of the opening 14. This also provides clearance for movement of the reflector in the Z direction.

It will now be clear that the present invention provides for X-Y positioning of the ellipsoidal reflector of a lithotripter with positive confirmation of the axis of the reflector being in alignment with the kidney stone through shadowing of the kidney stone by the radio-opaque disc 56 lying just below the x-ray apparatus, and fixed relative to the pedestal 20. Any physician, nurse, or x-ray technician with any skill in reading x-rays can readily confirm the position. If alignment is not precise, then is a simple matter to measure on the x-ray how far, and in what direction the pedestal should be moved for precise alignment. A second x-ray then may be taken to confirm perfect shadowing of the kidney stone 18 by the disc 56, thereby insuring that the axis of the reflector is aligned with the kidney stone.

It is to be understood that the specific example of the invention as herein shown and described is for illustrative purposes only. Various changes may occur to those skilled in the art, and will be understood as forming a part of the present invention insofar as they fall within the spirit and scope of the appended claims.

The invention is claimed as follows:

1. A lithotripter having an x-ray aiming system and comprising a table for supporting a patient having a kidney stone, said table having an opening therein with the patient located on said table so that the kidney stone is disposed above said opening, support means disposed below said table and being horizontally movable, a shock wave generator supported by said support means and including an upwardly opening truncated ellipsoidal reflector with a vertical axis and having a spark gap at the first focus point of the ellipsoidal reflector with the second focus point of the ellipsoidal reflector to coincide with the kidney stone, said support means being horizontally movable to align said vertical axis with the kidney stone, means for disposing an x-ray film in alignment with said table opening, x-ray apparatus disposed above said table and aligned with said opening for cooperating with the x-ray film to produce an x-ray picture, an x-ray opaque aiming member, means supporting said x-ray opaque aiming member from said first mentioned support means below said x-ray apparatus to produce a shadow on an x-ray picture, said x-ray opaque aiming member being fixed in alignment with said reflector vertical axis, said x-ray opaque aiming member thus shadowing said kidney stone when said vertical axis passes through said kidney stone and displaying in the event of misalignment how far and in what direction said supporting means must be moved to effect such shadowing and alignment.

2. A lithotripter as set forth in claim 1 wherein said x-ray opaque aiming member comprises an x-ray opaque disc.

3. A lithotripter as set forth in claim 1 and further including means for vertically moving said reflector relative to said first mentioned support means.

4. A lithotripter as set forth in claim 3 wherein said x-ray opaque aiming member comprises an x-ray opaque disc.

5. A lithotripter as set forth in claim 1 wherein said x-ray opaque aiming member support means comprises a rigid support secured to said first mentioned support means.

6. A lithotripter as set forth in claim 5 wherein said rigid support comprises a substantially C-shaped arm.

7. A lithotripter as set forth in claim 6 wherein said x-ray opaque aiming member comprises an x-ray opaque disc.

8. A lithotripter as set forth in claim 1 wherein said reflector has horizontal dimensions less than the horizontal dimensions of said opening in said table to permit movement of said reflector in said opening both horizontally and vertically.

* * * * *